United States Patent

Renshaw

[11] Patent Number: 6,017,476
[45] Date of Patent: Jan. 25, 2000

[54] METHOD FOR EMBEDDING AND SECTIONING SPECIMEN

[76] Inventor: Anthony A. Renshaw, 315 W. 23rd St., Apt. 9F, New York, N.Y. 10011

[21] Appl. No.: 08/933,659

[22] Filed: Sep. 19, 1997

Related U.S. Application Data

[60] Provisional application No. 60/026,350, Sep. 19, 1996.

[51] Int. Cl.[7] .................................................. B29C 39/10
[52] U.S. Cl. .......................... 264/158; 264/263; 264/274; 264/275; 264/279.1; 425/117; 600/564; 83/915.5
[58] Field of Search ..................... 264/158, 274, 264/279.1, 275, 263; 425/117; 428/67; 600/562, 564; 83/915.5

[56] References Cited

U.S. PATENT DOCUMENTS

| | | |
|---|---|---|
| 1,065,040 | 6/1913 | Garner . |
| 2,996,762 | 8/1961 | McCormick . |
| 3,319,289 | 5/1967 | McCormick . |
| 3,411,185 | 11/1968 | Pickett . |
| 3,456,300 | 7/1969 | Pickett . |
| 3,674,396 | 7/1972 | McCormick ............................ 425/117 |
| 3,940,219 | 2/1976 | Picket . |
| 3,982,862 | 9/1976 | Pickett et al. ............................ 425/117 |
| 4,141,312 | 2/1979 | Louder . |
| 4,421,246 | 12/1983 | Schultz . |
| 4,549,670 | 10/1985 | Trendler . |
| 4,557,903 | 12/1985 | McCormick ............................ 422/101 |
| 4,569,647 | 2/1986 | McCormick . |
| 4,752,347 | 6/1988 | Rada . |
| 4,801,553 | 1/1989 | Owen . |
| 4,822,495 | 4/1989 | Michels . |
| 4,893,424 | 1/1990 | McLean . |
| 5,061,452 | 10/1991 | Yamamoto . |
| 5,080,869 | 1/1992 | McCormick . |
| 5,127,537 | 7/1992 | Graham . |
| 5,139,951 | 8/1992 | Butz . |
| 5,260,985 | 11/1993 | Mosby . |
| 5,269,671 | 12/1993 | McCormick . |
| 5,312,758 | 5/1994 | Ahlqvist . |
| 5,358,692 | 10/1994 | Reynolds . |
| 5,416,029 | 5/1995 | Miller . |
| 5,424,040 | 6/1995 | Bjornsson . |
| 5,532,168 | 7/1996 | Mazantz . |
| 5,543,114 | 8/1996 | Dudek . |
| 5,612,218 | 3/1997 | Busch et al. ............................ 435/288.1 |

*Primary Examiner*—Jan H. Silbaugh
*Assistant Examiner*—Edmund H. Lee
*Attorney, Agent, or Firm*—Richard J. Birch

[57] ABSTRACT

A specimen processing method and cassette utilizes an open-topped, perforated collection cradle (12) and a flat, perforated embedding pedestal (10) which snap together in a male/female relationship to enclose and orient a specimen (14) during chemical processing. After chemical processing, the embedding pedestal (10) enables a specimen to be embedded in exactly the same plane as the cutting plane of a microtome during sectioning. This minimizes the number of sections required for histologic evaluation and eliminates the need for mechanical handling of the tissue specimen after its initial collection.

6 Claims, 6 Drawing Sheets

METHOD FOR EMBEDDING AND SECTIONING SPECIMEN

CROSS-REFERENCE TO RELATED APPLICATION

The application claims the benefit of U.S. Provisional Application Ser. No. 60/026,350 filed Sep. 19, 1996.

BACKGROUND

1. Field of Invention

This invention relates to a method for collecting, processing, embedding, and microtome sectioning of biopsy tissue specimens and a processing cassette for use therein.

2. Description of the Prior Art

Preparation of tissue specimens for histological examination currently involves extensive manual manipulation of the tissue and tissue fragments. This manipulation is labor intensive, costly, and prone to human error. Furthermore, the manipulation does not preserve the integrity and spatial positioning of the tissue specimen throughout chemical processing and embedding. Tissue integrity and spatial positioning relative to the eventual cutting plane of the microtome are important for histological evaluation of the tissue since all tissue fragments must be visually assessed. If the tissue does not lie on the same plane, then several sections of the tissue must be taken and made into separate slides for evaluation. Each of these different slides will have a different part of the original tissue sample and will need to be separately evaluated by the pathologist. Pathologic examination can be significantly improved and the cost reduced if a single slide of the tissue includes a complete section of the original biopsy in the same shape and relative order (if fragmented) as the original biopsy.

When a biopsy is first obtained from a patient in the operating room, it is normally placed in a temporary storage container filled with a tissue preserving solution or fixative. No control is exerted on the spatial orientation or integrity of the tissue while in the fixative, and tissue samples twist, bend, and fragment. Some tissue sampling techniques produce tissue samples with a specific geometry. For example, core needle biopsies produce a cylindrical tissue sample generally 1 to 3 mm in diameter and up to 2 cm long. The geometry of such tissue samples can be significantly distorted at this stage of the tissue processing.

The distorted and fragmented tissue in the fixative is then sent to pathology where it is placed by hand into a tissue processing cassette. Tissue processing cassettes are normally perforated, box-like structures with hinged or removable tops that enclose a tissue specimen during chemical processing. The cassette also has a surface on which patient and tissue information can be easily imprinted or written. Specimens within the individual cassettes are immersed in a series of chemical baths and rinses to prepare the tissue for examination. This treatment can include, for example, fixing and dehydrating. This process takes several hours and is normally performed by an automated machine which can process many tissue samples at the same time. Cassettes are generally made of a moldable plastic that is inert to the chemical reagents used to process the tissue and the tissue itself.

The cassette perforations must be both large enough to allow the chemical reagents to fully contact the tissue and permit trapped air to escape and small enough to prevent small tissue fragments from being washed out of the cassette. In some cases, the tissue and tissue fragments are so small that they must be wrapped in filter paper or some other medium to prevent their loss during processing. Perforations in the prior art have evolved from a regular series of holes in the top or bottom of the cassette such as taught in U.S. Pat. Nos. 3,411,185, 3,456,300, 3,674,396, and 3,982,862 to a regular series of grooves in the top, bottom, and sides of the cassette such as taught in U.S. Pat. No. 4,421,246. A cassette with a meshed enclosure for very small particles is described in U.S. Pat. No. 5,427,742. A cassette with two separate collection chambers with different size perforations is disclosed in U.S. Pat. No. 5,543,114.

Once the chemical processing is completed, a technician removes the tissue and tissue fragments from the cassette by hand and places them in a mold. If the tissue has been wrapped in filter paper or some other medium, this must be manually removed. If there are many tissue fragments, each must be placed into the mold. In addition, if the original tissue specimen had a particular geometry, the technician may attempt to meticulously arrange the tissue fragments in the mold in the same order as the original geometry. Or, if the pathologist wishes to section a tissue sample beginning from one particular face or side of the tissue, the technician must arrange the tissue sample with that particular face or side on the bottom of the mold.

In order to facilitate the manual arrangement of the tissue sample in the bottom of the mold, a few drops of molten wax, or paraffin, or similar embedding material may be placed in the bottom of the mold and allowed to partially harden before the tissue is placed in the mold. The partially hardened wax helps hold the tissue fragments in position as the technician manipulates the specimen with forceps or tweezers. In addition, this thin layer of wax helps prevent the tissue from sticking to the mold.

Once the tissue sample has been properly arranged, molten wax, paraffin or similar embedding medium is poured into the mold and over the tissue and allowed to harden. The open-topped box-like part of the cassette is normally placed on top of the mold and tissue specimen during this operation so that the bottom of the cassette becomes embedded in the same paraffin block as the tissue specimen. This allows the patient and tissue information to be permanently attached to the tissue specimen. Once the paraffin or wax has hardened, the paraffin block together with the tissue and the base of the cassette are removed from the mold. The base of the cassette fits into the clamp of a standard microtome for sectioning of the specimen into thin slices which are mounted on slides for histologic evaluation.

The standard collection, processing, and embedding procedures for biopsy tissue specimens suffer from several disadvantages that increase the difficulty and cost of histologic evaluation.

a. First, the specimen is often not aligned in the same plane as the cutting plane of the microtome. A principal cause of misalignment is the fact that the reference plane for the flatness or planarity of the tissue sample during embedding is not the same as during sectioning. During embedding, the reference plane is the bottom of the embedding mold. During sectioning, the reference plane is the base of the cassette as mounted in the microtome. The base of the cassette is meant to be aligned flat with respect to the bottom of the mold during embedding, but small misalignments can easily occur. Furthermore, even if the cassette and the mold are perfectly aligned, the tissue may not be flat with respect to the bottom of the mold, especially if a thin layer of positioning wax has been placed between the tissue and the mold. Since the sections sliced by the microtome are normally 5 microns thick, small misalignments during embedding can greatly reduce the amount of tissue present on each section, especially for small tissue fragments. Tissue fragments as small as 50 microns in diameter are now commonly evaluated. Additional sections must be prepared and evaluated by the pathologist when the initial sections do not have enough tissue. Sections with valuable tissue may be inadvertently overlooked and not evaluated. This is expensive, time consuming, and inefficient.

b. The shape and orientation of tissue samples with a specific geometries are not preserved during processing, and, if the tissue fragments are re-ordered by hand, may even be reversed during processing. For example, with skin punch biopsies it is important to section the tissue perpendicular to the epidermis, not parallel, so that the epidermis is visible in each section.

c. Each tissue sample is mechanically handled at least twice after initial collection: once in transferring the tissue from the collection container to the cassette, and once when transferring and orienting the tissue in the base of the mold. When the tissue sample fragments, each fragment must be manually manipulated. Particularly small fragments may need to be wrapped in filter paper for processing. This increases the cost and time of histologic evaluation and greatly increases the likelihood of human error and inaccurate diagnosis.

d. Small biopsies may be difficult to find and possibly lost during processing.

U.S. Pat. No. 5,424,040 to Bjornsson discloses a tissue specimen collection kit which permits tissue specimens to be collected in the operating room and then chemically processed and embedded without mechanical handling. However, since tissue is collected in the bottom of a concave mesh membrane in order to concentrate the tissue cells, the spatial geometry of the biopsy is destroyed and geometric diagnostic indicators are lost. There is no reference plane in the sections taken from this device. Furthermore, since the tissue is embedded in paraffin within the concave mesh membrane, sectioning requires either peeling the membrane off the paraffin block or sectioning directly through the mesh. Peeling the membrane off the paraffin block may remove valuable tissue that is either stuck to the membrane or breaks away from the paraffin during the peeling off process. Sectioning directly through the membrane will quickly dull the microtome blade and will produce jagged, poorly cut sections. The cell collection device disclosed by Ahlqvist in U.S. Pat. No. 5,312,758 suffers similar problems.

U.S. Pat. No. 4,801,553 to Owen et al. discloses a tissue cassette that holds tissue specimens in an oriented position during processing and embedding without handling or repositioning the specimen. However, embedding requires a complicated two step procedure in which an initial layer of paraffin is solidified to plug the leaks in the cassette before the entire specimen and cassette can be embedded. In order to section the paraffin block, sections of the original cassette must be strategically peeled away from the paraffin which may well remove valuable tissue. In addition, as with most cassettes, the reference plane for sectioning is not the same as for embedding which can easily lead to specimen misalignment. The cost of such a cassette is also likely to be high since it involves not only tear away construction but also a complicated resilient hinge structure to secure arbitrarily shaped tissue specimens during processing.

U.S. Pat. No. 5,437,742 to Holland depicts a tissue processing cassette in which the tissue specimen is manually removed from the cassette and placed into a mold adapted to receive the cassette base in the upper section of the mold. The tissue specimen is thus located below the cassette base prior to embedding the specimen in paraffin. The reference plane for embedding is therefore not the same plane used for sectioning.

OBJECTS AND ADVANTAGES

It is an object of the invention to provide a tissue processing method and cassette in which the reference planes of the tissue sample during embedding and sectioning are the same.

It is another object of the invention to provide a tissue processing method and cassette that preserves the spatial geometry and orientation of any tissue fragments during processing and embedding.

It is another object of the invention to provide a tissue processing method and cassette that minimizes mechanical handling during specimen collection, chemical processing, and embedding and reduces the cost of biopsy preparation.

It is another object of the invention to provide a tissue processing method and cassette that reduces the likelihood of losing tissue and tissue fragments during preparation and sectioning and also reduces the chances of human error.

These are other objects of the present invention will be more fully understood from the following detailed description of the invention with reference to accompanying drawings.

BRIEF SUMMARY OF THE INVENTION

A specimen is positioned above a planar, perforated element that is positioned on and forms a portion of an embedding pedestal. All portions of the planar, perforated element lie below the specimen. The planar, perforated element defines a reference plane with respect to the specimen. The specimen and at least a portion of the embedding pedestal are embedded in an embedding medium to form an integral embedded unit with the specimen remaining above the planar, perforated unit. Thereafter, the integral embedded unit is sectioned in at least one plane that passes through the embedded specimen and is in registered relationship to the reference plane.

REFERENCE NUMERALS IN THE DRAWINGS

10—an embedding pedestal or cover of the cassette
12—a collection cradle or receptacle of the cassette
14—a tissue specimen
16—a flat, perforated or meshed surface on 10
18—supporting spans lying entirely underneath 16 and maintaining its flatness
20—a peripheral wall projecting downward away from 16 at an angle
22—perforations, holes, or grooves in 20

24—a set of walls defining the outer frame of 10
26—a slanted surface on 24 for imprinting patient and biopsy information
28—a perforated or meshed surface inside 12
30—slanted walls projecting outwards from the edges of 28
32—perforations, holes, or grooves in 30
34—a rectangular frame attached to the ends of 30
36—a projecting ledge on the collection cradle
38—a span on 10 for engaging 36
40—alignment struts on 12
42—latch on 12
44—latch engagement lip on 10
46—a cylindrical tissue specimen
48—a groove separating 16 into two separate meshes
50—a mating groove separating 28 into two separate meshes
52—a base plug or stand for embedding
54—a rectangular skirt on 52
56—a raised, mating plug on 52
58—a rectangular frame for embedding
60—a rectangular rim on 58
62—a rectangular frame on 58
64—solidified paraffin

DETAILED DESCRIPTION OF THE DRAWINGS

Figure 1:
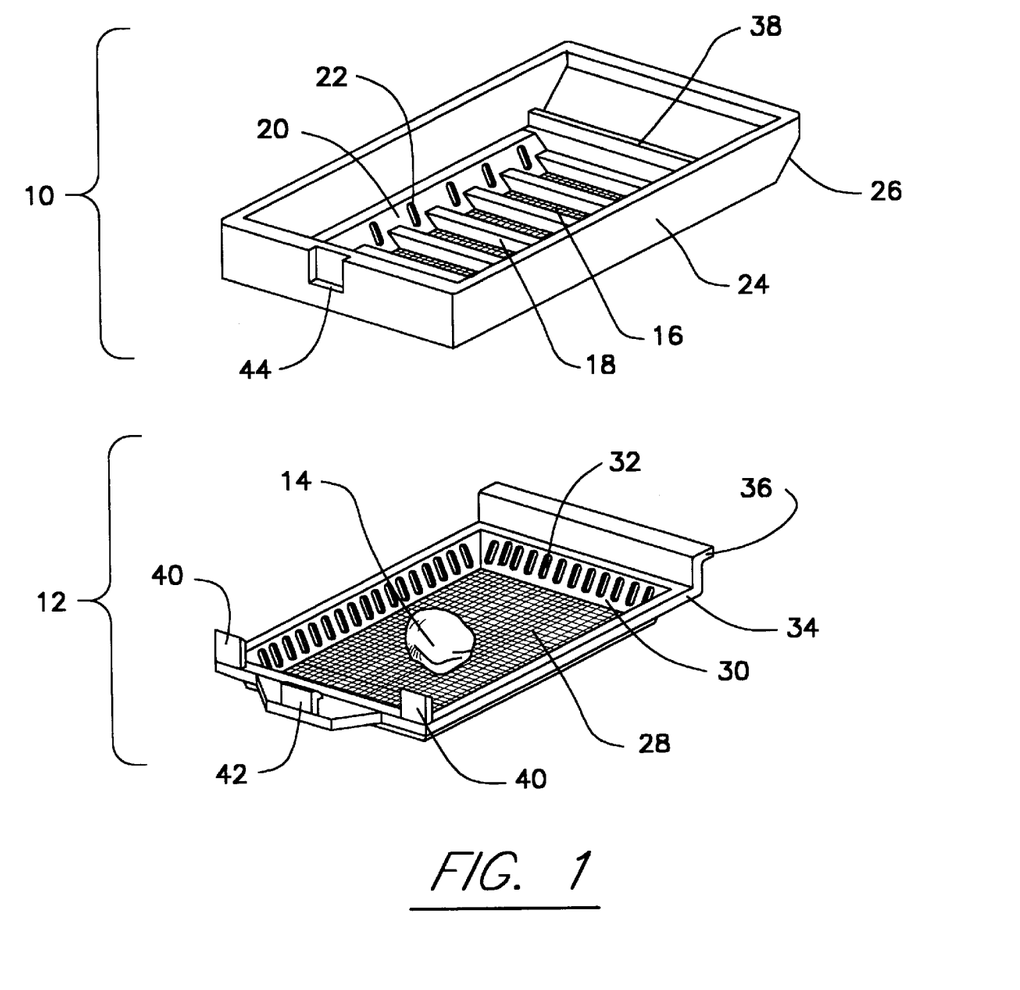
FIG. 1 is a perspective view of a cassette according to the present invention in position for tissue collection.
Figure 2:
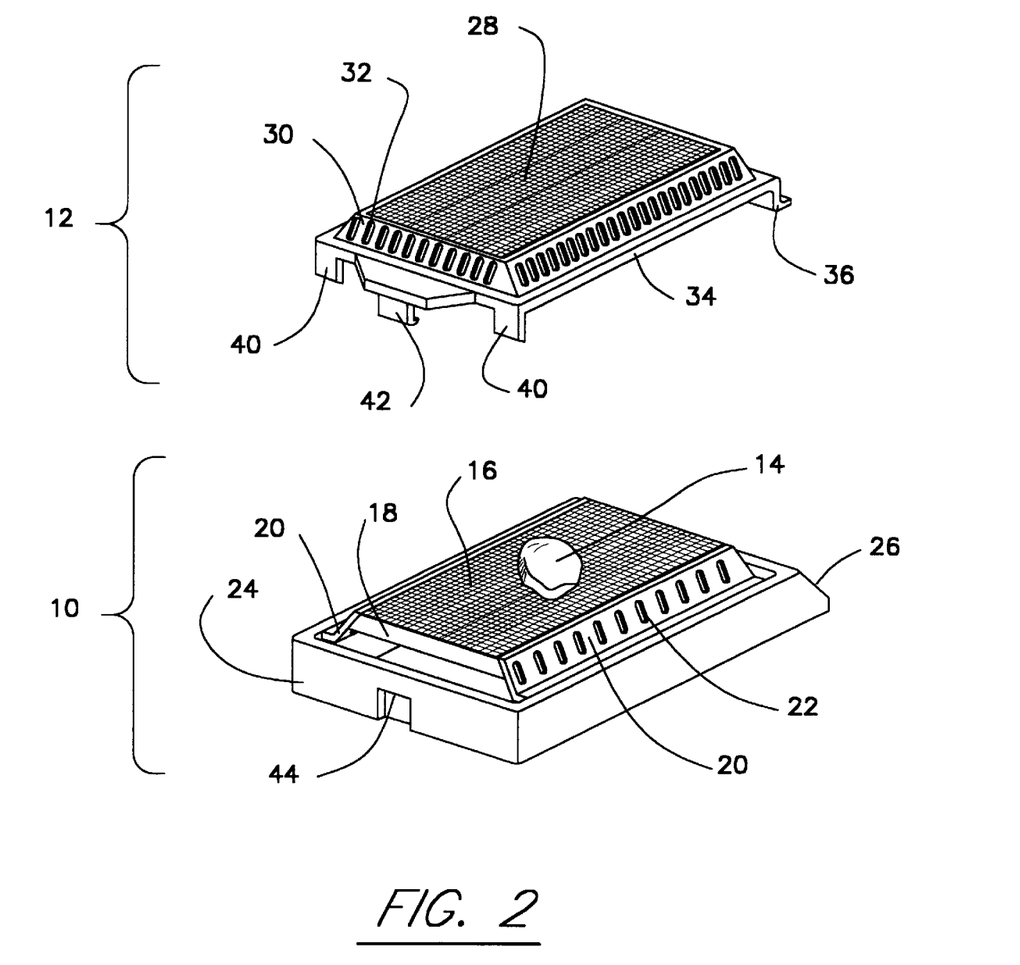
FIG. 2 is a perspective view of a cassette according to the present invention in position for tissue embedding.
Figure 3:
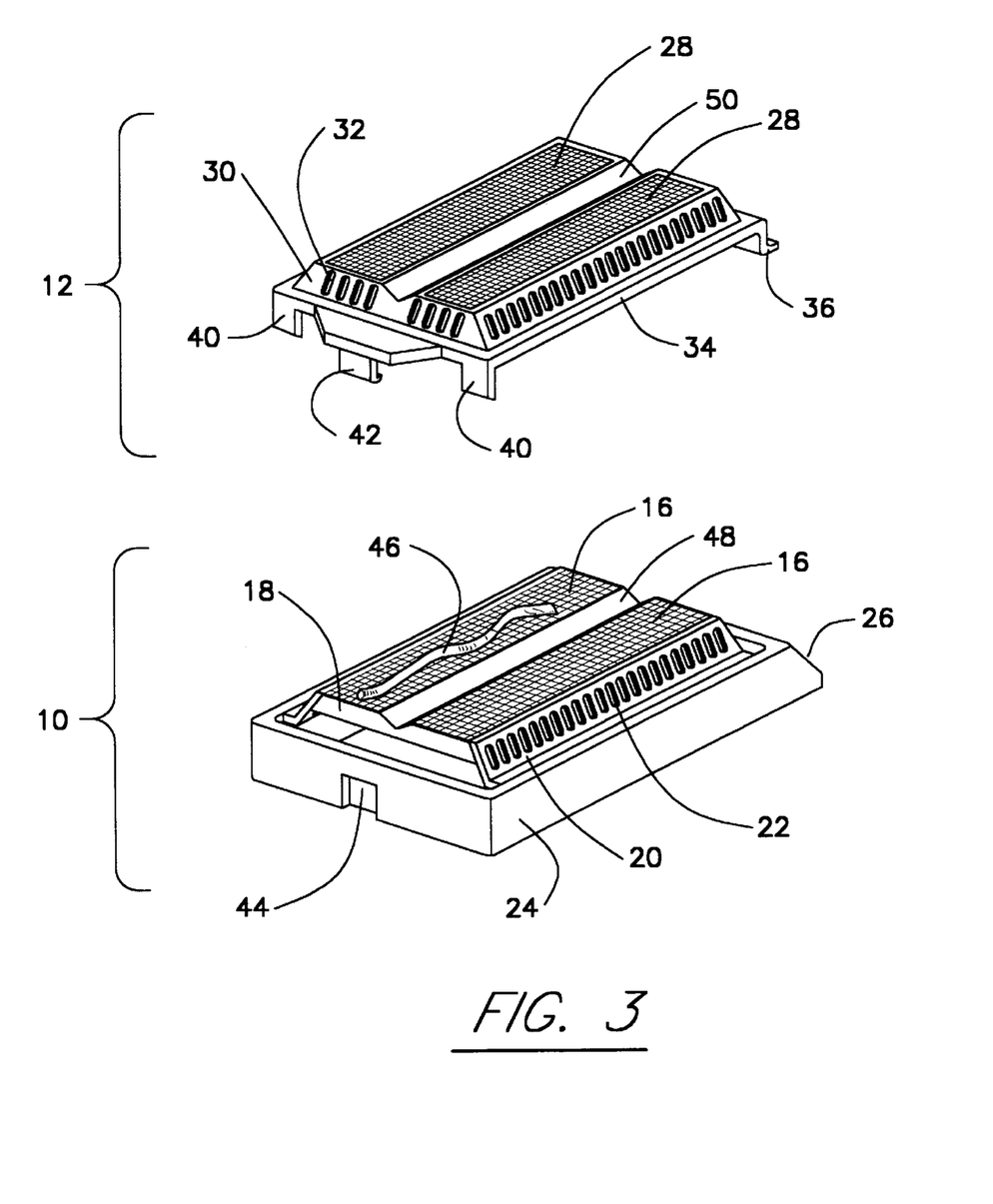
FIG. 3 is a perspective view of another embodiment of a tissue cassette according to the present invention.

The cassette comprises an embedding pedestal or cover 10 and a collection cradle or receptacle 12. FIG. 1 shows 10 and 12 in position for collection and entrapping a tissue specimen 14. In this view, the collection cradle 12 is below the embedding pedestal 10 and the tissue sample 14 is retained within the cradle by gravity. FIG. 2 shows 10, 12 and 14 in position for embedding. In this view, the embedding pedestal 10 is below the collection cradle 12 and the tissue specimen 14 lies on 10. FIG. 3 shows a second embodiment of the invention comprising modified versions of 10 and 12 for use with one or more tissue specimens 46 possessing a specific geometry.

Referring to FIGS. 1, 2, and 3, the embedding pedestal 10 has a flat, perforated or meshed surface 16. The flatness or planarity of 16 can be partially maintained by supporting spans 18 which lie entirely underneath 16 on the interior side of 16. Two peripheral walls 20 project downward away from 16 at an angle and serve as mounting locations for 18. The two walls 20 are perforated with holes or grooves 22 which are large enough to permit chemical reagents and air bubbles to pass through but small enough to retain tissue fragments. The ends of walls 20 not attached to 16 are joined to a set of walls 24 that define the outer frame of the 10. 24 is nominally rectangular and designed to be easily attached to a standard microtome. One of these walls 24 is 26 and is angled and defines a convenient surface for imprinting patient and biopsy information.

Figure 5A:
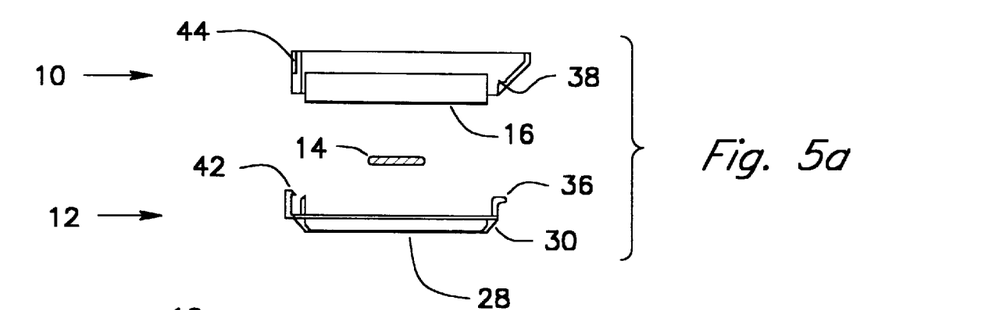
FIGS. 5A–5F are a series of views showing stages in the use of the cassette.
Figure 5B:
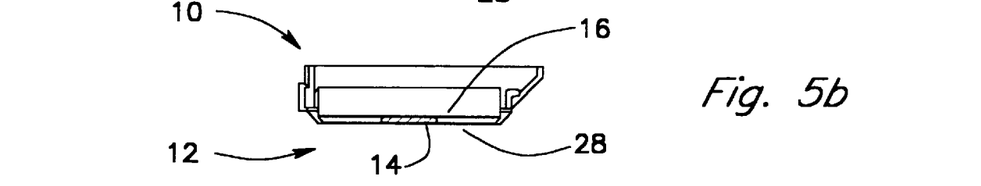

The collecting cradle 12 also has a flat, meshed or perforated surface 28. The four edges of this surface are attached to four, slanted walls 30 that project away from 28. Each of these walls possess perforations, holes or grooves 30. The other ends of 30 are attached to a rectangular frame 34. At one end of 34, a projecting ledge 36 projects away from 34. 36 mates with a span 38 on the embedding pedestal 10 in a hinge-like fashion as shown in FIGS. 5a and 5b. The collection cradle 12 has two alignment struts 40 and a latch 42. 42 mates with the latch engagement 44 lip on 10. Unlike the flat mesh 16 on the embedding pedestal 10, the mesh surface 28 on the collection cradle 12 does not have any supporting spans to preserve its flatness. 28 may deform as necessary to secure different size tissue samples.

The embedding pedestal 10 fits into the collection cradle 12 in a male/female relationship wherein the flat meshed surface 16 of 10 which lies entirely above the walls 24 of 10 fits entirely inside the walls 30 of 12. The male, protruding design of 10 positions the tissue sample 14 so that it can be sectioned without interference from 10. The female, enclosing design of 12 facilitates initial collection of 14.

Referring to FIG. 3, in a second embodiment of the cassette, a groove 48 divides 16 into two separate flat, perforated or meshed sections. A similarly shaped groove 48 divides 28 into two separate, flat, perforated or meshed sections. The shape of each separate meshed section approximately matches the shape of the cylindrical tissue specimen 46 in that is it long and narrow.

Figure 4:
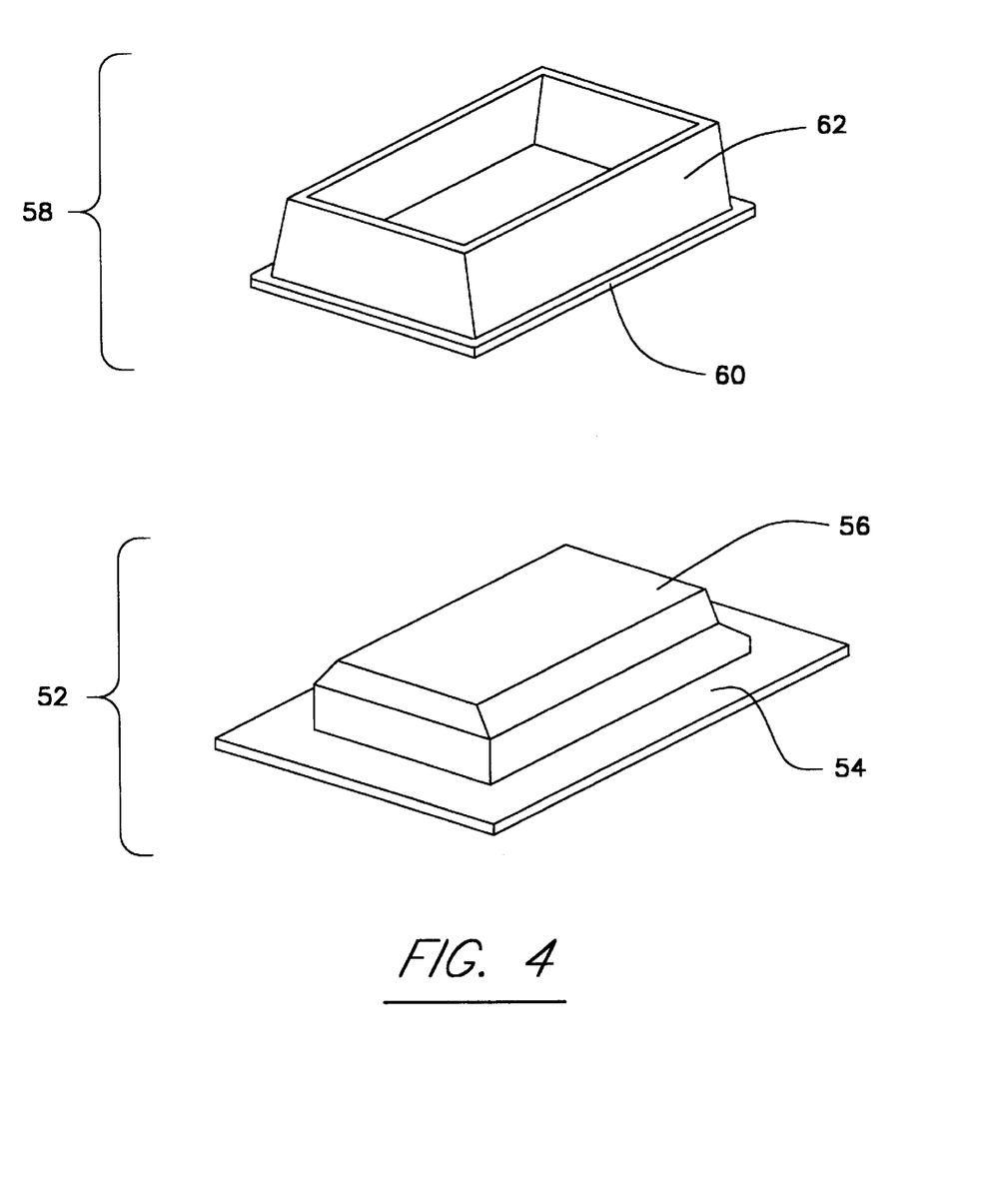
FIG. 4 is a perspective view of an embedding apparatus for use with the present invention.

FIG. 4 shows an embedding apparatus for use with the cassette comprising a base embedding stand 52 and a rectangular frame 58. 52 is composed of a rectangular skirt 54 and a raised plug 56. The shape of 56 is designed to fit snugly into the interior of 10. The rectangular skirt 54 is large enough to extend outwards beyond the outer frame 24 of 10. 58 is composed of a rectangular rim 60 and a rectangular frame 62 that projects upwards from 60. The rim fits snugly over the rectangular frame 24.

The collection cradle 12 and embedding pedestal 10 may be made from an inert moldable plastic. The base embedding stand 52 and embedding frame 58 may be made from any number of materials which are impermeable to paraffin, retain their shape, and normally do not stick to paraffin. This list of materials includes inert moldable plastic or stainless steel.

Operation

A representative sequence of operations will now be described with reference to FIG. 5. FIG. 5a shows the embedding pedestal 10, the collection cradle 12, and a specimen 14 in position for specimen collection. The tissue specimen 14 is expelled into the cradle 12 as soon as it is collected in the operating room. The four slanted sides of the cradle 30 prevent the tissue from accidentally falling out of the cassette and allow the tissue to be easily flushed onto the meshed or perforated surface 28 using saline or a fixative if necessary. Once the tissue has been collected and lies entirely on 28, the embedding pedestal 10 is placed over the cradle 12 in the manner of a cover. This is accomplished by have the projecting ledge 36 of 12 slipped over the span 38 of 10. 10 is then rotated downwards as if hinged by 36 and 38 onto 12 where the latch 42 of 12 engages the engagement lip 44 and securely fastens 10 to 12. This secured position is shown in FIG. 5b.

When 10 and 12 are properly engaged to form an integral unit as shown in FIG. 5b, a small space will exist between the two meshed or perforated surfaces 16 and 28. The specimen 14 will be trapped in this space by 16 and 28 and the slanted walls 30 of the collection cradle. Ideally, the specimen will be held in a fixed position between 16 and 28. Hence, the space between 16 and 28 will be designed for normal tissue specimen sizes. If the specimen is large, 28 may deform outwards to accommodate the specimen. 16, however, will remain flat because of the supporting spans 18 lying on the opposite side of the 16 from the specimen. If the specimen is small, there may be some movement of the specimen while it is in the space between 16 and 28. However, because the space is small, this motion will be limited and will minimize the unrestrained motion and distortion of the tissue sample.

Figure 5C:
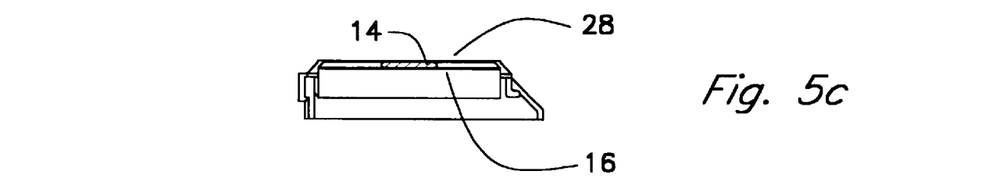
Figure 5D:
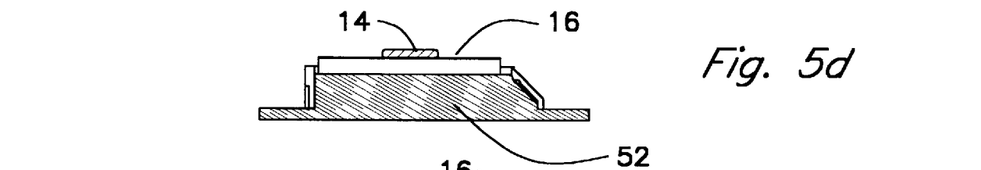
Figure 5E:
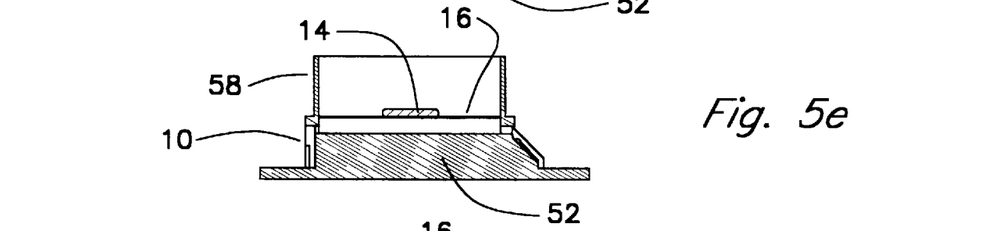
Figure 5F:
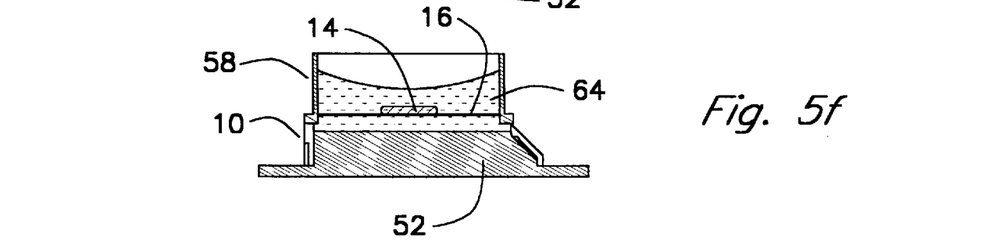

The tissue specimen 14 is chemically processed in the usual manner while entrapped between 10 and 12. The meshes and perforations 16, 28, 22, 32 allow the chemical reagents to fully contact the specimen without losing any tissue fragments or trapping air bubbles. After chemical processing, the cassette is inverted from its orientation during collection so that the embedding pedestal is below the collection cradle as shown in FIG. 5c. The cassette is place on the base of the embedding apparatus 52 which fits snugly into the cavity of the cassette. The collection cradle 12 is then carefully removed as shown in FIG. 5d. The tissue specimen(s) remain on top of the flat mesh or perforated surface 16. The rectangular frame for embedding 58 is then placed over the cassette as shown in FIG. 5e.

Molten paraffin is then poured into the open top of the assembly. The paraffin flows down past the specimen and through 16 but is stopped by the embedding base 52. Enough paraffin is poured into this mold to completely cover the specimen. The paraffin is then allowed to harden into a solidified plug 64. Ideally the paraffin will harden from the bottom upwards. This can be achieved, for example, by placing the embedding stand on a cooling surface as described in U.S. Pat. No. 4,801,553. Since the solidified paraffin has less volume than the molten paraffin, the solidifying paraffin will move downwards as it solidifies leaving a meniscus at the top. This downwards motion of the solidifying paraffin will further draw the tissue specimen flat against 16. As a consequence of the specimen being held flat against the flat surface 16 by both gravity and the solidifying paraffin, the tissue specimen will be automatically aligned in the same plane as 16 without mechanical manipulation or special handling or care by the technician.

Once the paraffin has hardened, both pieces of the embedding frame, 52 and 58 are removed. The cassette and embedded paraffin are then mounted in a microtome for sectioning in the usual manner. Since the tissue is above the entire cassette, sections can be taken directly from the top surface of the paraffin without interference from the cassette and without having to remove any portion of 10. Since the specimen has been held in the same plane as 16, and the reference plane during section is always parallel relative to 16, sections will include tissue from the entire tissue specimen. In this manner, the tissue is oriented flat relative to the cutting plane of the microtome without handling, repositioning, or reorienting the tissue specimen during processing.

A major advantage of the present invention is its automatic alignment of the tissue specimen 14 in the cutting plane of the microtome by virtue of gravity and the downward flow of paraffin during solidification. Since the flat mesh 16 upon which the specimen rests during embedding is part of the same piece that is secured in the chuck of the microtome during sectioning, the alignment of this surface relative to the cutting plane of the microtome is excellent. All known prior art embeds the tissue specimen 14 in the bottom of a mold which is not attached to the chuck of the microtome in any way. In addition, the tissue specimen 14 may not lie flat against the bottom of the mold if paraffin lies between the mold and the tissue specimen. The potential for misalignment is greatly magnified in the prior art by aligning the tissue specimen to a layer of paraffin, which in turn is aligned with a mold, which in turn is aligned to the cassette.

The tissue can also be embedded in paraffin in a position flat relative to 16 using other embedding devices besides 52 and 58. For example, the tissue 14 and embedding pedestal 10 can be positioned between two L-shaped pieces of lead which form a mold around 10 and 14 as described in U.S. Pat. No. 2,996,762. The molten paraffin is poured into the open top of this mold and the heavy side walls of lead are removed after the paraffin hardens.

Tissue samples that need to be sectioned beginning from one specific surface can be easily prepared by initially enclosing the specimen with the first surface to be sectioned flat against 28, the meshed or perforated surface of the collection cradle. In this manner, pathologist need not mark preferred sides of the tissue or worry about reorienting the tissue during normal processing and embedding. He or she need only properly align the specimen when it is initially collected.

Figure 6:
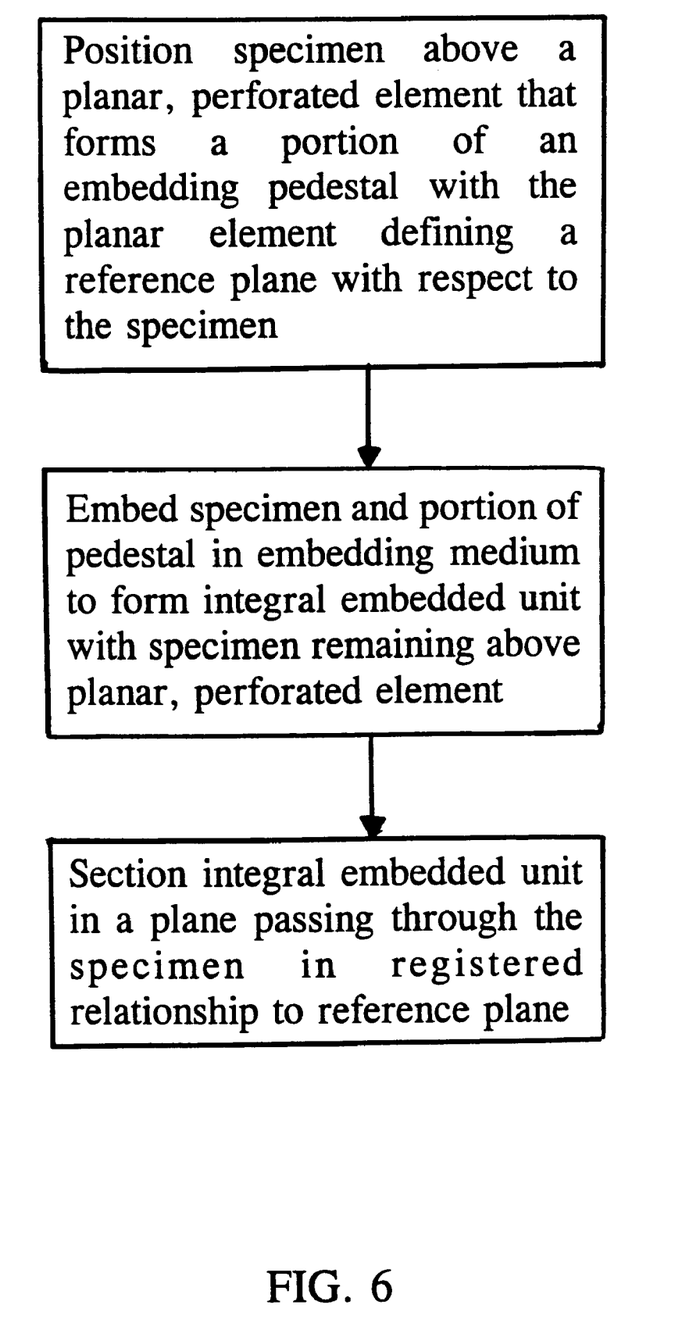
FIG. 6 is a flow diagram of the method of the invention.

FIG. 6 illustrates in block flow form the broad steps of the method of the invention. The specimen, such as a tissue specimen, is postioned above a planar, perforated element that forms a portion of an embedding pedestal with the planar perforated element defining a reference plane with respect to the specimen. The specimen and at least a portion of the pedestal are embedded in an embedding medium to form an integral embedded unit. The unit can then be sectioned with at least one sectioning plane passing through the specimen in registered relationship to the defined reference plane.

Although the invention has been described with reference to particular materials and configurations, it is only to be limited so far as is set forth in the appended claims.

I claim:

1. A method for embedding and sectioning a specimen comprising the steps of:

(a) positioning the specimen above a planar, perforated element that is positioned on and forms a portion of an embedding pedestal that has all portions of the planar, perforated element lying below the specimen, said planar perforated element defining a reference plane with respect to the specimen;

(b) embedding the specimen and at least a portion of the embedding pedestal in an embedding medium to form an integral embedded unit with the specimen remaining above the planar, perforated element; and, (c) sectioning the integral embedded unit in at least one plane that passes through the embedded specimen and is in registered relationship to said reference plane.

2. The method of claim 1 wherein said specimen is positioned on top of and in physical contact with said planar, perforated element.

3. The method of claim 1 wherein said specimen is positioned on top of, but not in physical contact with said planar, perforated element.

4. A method for embedding and sectioning a tissue specimen for microtome sectioning comprising the steps of:

(a) positioning the tissue specimen above a planar, perforated element that is positioned on and forms a portion of an embedding pedestal that has all portions thereof lying below the tissue specimen, said planar perforated element defining a reference plane with respect to the tissue specimen;

(b) embedding the tissue specimen and at least a portion of the embedding pedestal in an embedding medium to form an integral embedded unit with the tissue specimen remaining above the planar, perforated element;

(c) mounting the integral embedded unit on a microtome with the reference plane parallel to a cutting plane of the microtome; and, (d) sectioning the embedded tissue specimen with the microtome.

5. The method of claim 4 wherein said tissue specimen is positioned on top of and in physical contact with said planar, perforated element.

6. The method of claim 4 wherein said tissue specimen is positioned on top of, but not in physical contact with said planar, perforated element.

* * * * *